United States Patent [19]
Gaboury et al.

[11] Patent Number: 6,147,225
[45] Date of Patent: Nov. 14, 2000

[54] THIACROWN ETHER COMPOUND

[75] Inventors: Janet A. Gaboury, Blue Bell; Fu Chen, Newtown, both of Pa.

[73] Assignee: Betzdearborn Inc., Trevose, Pa.

[21] Appl. No.: 09/088,991

[22] Filed: Jun. 2, 1998

[51] Int. Cl.[7] .......................... C07D 331/02; C08G 73/06
[52] U.S. Cl. ................................ 549/1; 528/424
[58] Field of Search .................. 549/1; 528/424

[56] References Cited

U.S. PATENT DOCUMENTS

| | | | |
|---|---|---|---|
| 3,856,813 | 12/1974 | Pedersen | 549/1 |
| 5,049,201 | 9/1991 | Cheng et al. | 134/42 |
| 5,071,581 | 12/1991 | Cipriano | 252/77 |
| 5,633,125 | 5/1997 | Martin | 430/398 |
| 5,891,956 | 4/1999 | Smith et al. | 525/56 |

FOREIGN PATENT DOCUMENTS

WO 96/38493   12/1996   WIPO .

OTHER PUBLICATIONS

Li et al, "Mass spectral analyses on a series of crown thio ethers", CA101:72076, 1984.

Guyon et al., "Lipophilic polythiamacrocycles as palladium extracting agents", Tetrahedron vol. 51, No. 14, pp. 4065–4074 (1995).

Saito et al., "Synthesis of thiacrown ether carboxylic acids and their characteristics as extractants for metal icons", Analytica Chimica Acta 299 (1994) 137–144.

Rogowski et al., "Intramolecular interactions between sulfur atoms in cyclotetrathioether radical cations", J. Chem., Soc. Perkin Trans. 2 (1994), pp. 779–783.

Buter et al., "Functionalized thia crown ethers. Synthesis, structure, and properties", J. Chem. Soc., Chem. Commun. (1990), vol. 3, pp. 282–284.

Patent abstracts of Japan, vol. 4, No. 46 (C–006) Apr. 10, 1980.

Patent abstracts of Japan, vol. 11, No. 43 (C–402) Feb. 7, 1987.

Patent abstracts of Japan, vol. 6, No. 266 (C–142) Dec. 25, 1982.

Zhengang Zong et al. "Synthesis and Complexation Properties of Polystyrene Supported Polymeric Thiocrown Ether" Eur. Polym. J. vol. 34, No. 5/6, 1998, pp. 761 to 766.XP 004139500 Great Britain.

H. Thijs Stock et al. "Synthesis of Enantiomerically Pure Thiocrown Ethers Derived from 1,1'–Binaphthalene–2, 2'–dio" Journal of Organic Chemistry, vol. 61, No. 9, 1996, pp. 3093 to 3105, XP 002124825, Columbus Ohio.

Patent Abstract of Japan, vol. 11, No. 136 (C–419) Apr. 30, 1987.

"Syntheses and Chelating Properties of Polymer–Supported Macrocyclic Polythioethers", by Masao Tomoi, Osamu Abe, Nobutaka Takasu, Hiroshi Kakiuchi, *Makromol. Chem.* 184, p 2431–2436 (1983).

"Syntheses of thiacrown ethers polymers and their application for heavy metal ion adsorbents" by Keiji Yamashita, Kyouzou Kurita, Kazumine Ohara, Kazutoshi Tamura, Mamoru Nango, Kazuichi Tsuda, *Reactive & Functional Polymers* 31, pp 47–55 (1996).

"Synthesis of macrocyclic sulfides using cesium thiolate: 1,4,8,11–tetrathiacyclotetradecane" by J. Buter and Richard M. Kellogg, *Organic Synthesis* vol. 65, pp. 150–158 (1987).

"Crystal and Molecular Structure of $(NbCl_5)_2(C_{10}H_{20}S_4)$. An Adduct of $NbCl_5$ with an "Inside out" Bridging Macrocyclic Ligand", by Richard E. DeSimone and Milton D. Glick, *Journal of the American Chemical Society* 97:4, pp. 942–943, Feb. 19, 1975.

*Primary Examiner*—Deborah C. Lambkin
*Attorney, Agent, or Firm*—Greenblum & Bernstein, P.L.C.

[57] ABSTRACT

Thiacrown ether and polymeric thiacrown ether compounds are disclosed. The thiacrown ether ring structures are substituted and have from 4 to about 10 sulfur atoms on each of the crown rings. The polymeric thiacrown ether ring structures are substituted with polymers and have from 4 to about 10 sulfur atoms on each of the crown rings. The thiacrown compounds of the present invention are expected to have utility in a wide range of applications including but not limited to utility as metal ion chelating, sequestering, and complexing agents. The thiacrown compounds are also expected to have utility as corrosion inhibitors for cooling tower, boiler, and waste water systems, hydrocarbon process systems and metal surface treatments systems.

9 Claims, No Drawings

THIACROWN ETHER COMPOUND

FIELD OF THE INVENTION

The present invention relates to heteromacrocyclic compounds and polymers containing said compounds. More particularly, the present invention relates to thiacrown ethers, and to polymers containing thiacrown ethers.

BACKGROUND OF THE INVENTION

Crown ethers are macrocyclic compounds in which oxygen atoms are separated by two or three carbon atoms. The name has been used for this class of compounds because of the resemblance of their molecular models to a crown. Since their discovery in the late 1960's, crown ethers have been intensively studied because of their cation complexing and binding abilities, especially to alkali and alkali earth cations. Crown ethers and compounds containing crown ethers are useful for a variety of applications, such as metal ion chelating and binding agents, catalysts for phase transfer reactions, encapsulating materials for electronic devices, and corrosion inhibitors in electronic packages and electrorheological fluid. Crown ethers are known to be useful as complexing agents for alkali and alkali earth cations, but are not particularly effective for complexing transition metal cations.

Thiacrown ethers are crown ethers in which the oxygen atoms are replaced with sulfur atoms as shown in Formula 1.

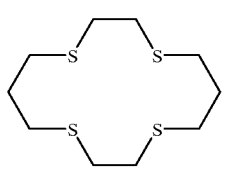

Formula 1

In contrast to the crown ethers, few applications have been explored for thiacrown ethers and their derivatives, although they are reported to form strong complexes with transition metal ions such as $Cu^{+2}$, $Fe^{+2}$, $Ni^{+2}$, $Co^{+2}$, $Hg^{+2}$ and $Ag^+$.

Due to increasingly stringent environmental regulation, the trend in industry has been to emphasize water reuse and recycling in order to minimize the discharge into the environment of water containing undesirable materials. Depending on the industrial system, it is often desirable to treat used process water to remove materials such as metals prior to recycling water or prior to discharging the used process water to the environment. In addition, in some industries such as in the photo developing industry, metals such as silver are valuable components which are typically recovered from used process streams prior to water discharge.

Thus, there is an ever present demand for new and efficient metal removal materials to facilitate the removal of metals from process streams prior to reuse or discharge.

Accordingly, an object of this invention to provide thiacrown ethers, polymeric thiacrown ethers to fulfill the desire for new and effective metal ion chelating, sequestering, and complexing agents and corrosion inhibitors.

PRIOR ART

J. Buter et. al. Organic Synthesis Vol. 65, pages 150–158 (1987) teaches the synthesis of thiacrown ether 1,4,8,11-tetrathiacyclo-tetradecane. The synthesis is conducted by first reacting 1,3-propane-dithiol with 2-chloroethanol to form 3,7-dithianonan-1,9-diol. This diol is reacted with thiourea to give 3,7-dithianonane-1,9-dithiol. The dithiol is then reacted with 1,3-dibromopropane to give 1,4,8,11-tetrathiacyclo-tetradecane.

Richard E. DeSimon et. al. proposes in J. Am. Chem. Soc. 97, 942 (1975) an "inside out" crystal structure involving the distortion of C-4 and C-5 carbon atoms in 1,4,8,11-tetrathiacyclotetradecane (abbreviated as 14-S-4) when it is forming a complex with $NbCl_5$ in benzene.

Masao Tomoi et. al. describes in Japan Kokai 55–19221 and Makromol. Chem. 184, pp. 2431–2436 (1983) a macrocyclic bound to a crosslinked polystyrene resin support. The polythiaethers are disclosed to be highly efficient adsorbents of Ag (I) and moderately effective adsorbants for Cu(II). The thiacrown ethers/macroporous polystyrene resins are disclosed as being in solid form and as being reuseable.

Keiji Yamashita et. al. describe in Reactive and Functional Polymers 31, 47–53 (1996) the polymerization and copolymerization of 6-(4'-vinylbenzyloxy)-1,4,8,11-tetrathiacyclotetradecane and 9-(4'-vinyl-benzyloxy)-1,4,7,14,17-hexathiacycloeicosane with styrene or N-vinylpyrrolidone. The polymers were studied for their ability to bind Ag(I) and Hg(II).

U.S. Pat. No. 5,071,581 to R. Cipriano discloses monomeric crown ethers (i.e., having only one crown ether in a molecule of the ether) and polymeric crown ethers (i.e., having at least one but possibly more crown ethers in a polymeric chain) wherein sulfur atoms replace oxygen atoms. The polymeric crown ethers are disclosed as being useful as a component of electrorheological fluid. The structure and configuration of the thiacrown compounds of the present invention are not disclosed.

WO 96/38493 discloses water-soluble polymers having particular formulas, functionalized by various groups. Thiocrown ethers are listed among the polymer substituents. The structure and configuration of the thiacrown compounds of the present invention are not disclosed.

SUMMARY OF THE INVENTION

To achieve the foregoing and other objects, the present invention provides substituted or unsubstituted thiacrown ethers, and polymers containing thiacrown ethers, having 4 to about 10 sulfur atoms in the crown ring. Unless specified otherwise, the term "thiacrown compound" is used herein to mean thiacrown ether and/or polymeric thiacrown ether compounds. The thiacrown ether compounds of the present invention are expected to have utility in a wide range of applications including but not limited to utility as metal ion chelating, sequestering, and complexing agents. The thiacrown compounds are also expected to have utility as corrosion inhibitors for cooling, boiler, and waste water systems, hydrocarbon process systems and metal surface treatments systems.

DETAILED DESCRIPTION OF THE INVENTION

The present invention provides new thiacrown compounds. The thiacrown ethers of the present invention have 4 to about 10 sulfur atoms in the crown ring, whether substituted or unsubstituted, and have the general formula:

Formula 2

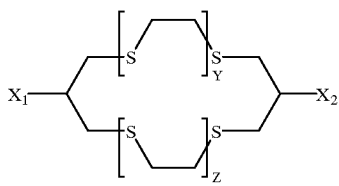

Formula 6

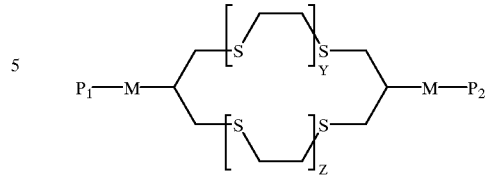

where Y is an integer of 1 to 7 and Z is an integer of 1 to 4 with the proviso that Y+Z cannot be greater than 8; $X_1$ and $X_2$ are independently H; SH; F; Cl; I; substituted or unsubstituted $C_1$ to $C_{10}$ linear or branched alkyl or alkenyl group; substituted or unsubstituted $C_6$ to $C_{10}$ aryl group; amine; mono- or di- $C_1$ to $C_{10}$ lower alkylamino; $C_1$ to $C_{10}$ lower alkanoylamino; nitro; cyano; COOH; $OCOR_1$ wherein $R_1$ is $C_1$ to $C_{10}$ alkyl or alkenyl group; $OR_2COOR_3$ wherein $R_2$ is substituted or unsubstituted $C_2$ to $C_5$ linear or branched alkyl group and $R_3$ is substituted or unsubstituted $C_1$ to $C_{10}$ linear or branched alkyl group or alkenyl group; $OR_4$ where $R_4$ is substituted or unsubstituted $C_1$ to $C_{10}$ linear or branched alkyl or alkenyl group; or $SR_5$ wherein $R_5$ is substituted or unsubstituted $C_1$ to $C_{10}$ linear or branched alkyl or alkenyl group; wherein the substituents of the $X_1$ and $X_2$ moieties are independently OH, SH, F, Br, Cl, I, COOH, amine, mono- or di- $C_1$ to $C_{10}$ alkylamino, alkanoylamino or nitro and with the proviso that both $X_1$ and $X_2$ cannot both be H.

The polymeric thiacrown ethers of the present invention have 4 to about 10 sulfur atoms, preferably have 4 to about 6 sulfur atoms in the crown ring and are thiacrown ethers attached directly to or linked with polymer chains or networks. The polymeric thiacrown ethers of the present invention have the formulas:

Formula 3

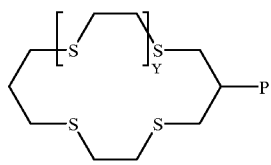

Formula 4

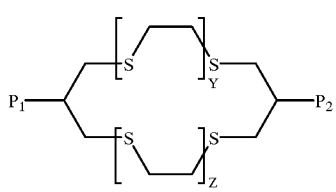

Formula 5

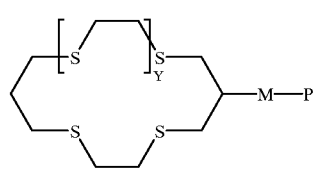

where in Y is an integer of 1 to 7, Z is an integer of 1 to 4 with the proviso that Y+Z cannot be greater than 8; M is a linkage between the thiacrown compound and the polymers P, $P_1$ and $P_2$ and M is O; COO where the carbon atom is attached to the polymer; $C_1$ to $C_5$ substituted or unsubstituted linear or branched alkylene wherein the substituent is OH, SH, F, Br, Cl, I, COOH, amine, mono- or di- $C_1$ to $C_5$ alkylamino, $C_1$ to $C_3$ lower alkanoylamino or nitro; or M is $NR_6$ where $R_6$ is H or $C_1$ to $C_5$ alkyl; or M is S with the proviso that the polymer cannot be polyethyleneimine. The polymeric thiacrown ethers of the present invention can be a polymer chain attached to one or more thiacrown moieties or the polymeric thiacrown ethers can be difunctional thiacrown moieties interconnecting polymers as illustrated in Formulas 4 and 6. The polymers P, $P_1$ and $P_2$ in Formulas 3–6 can be obtained from polymerization of monomers containing ethylenically unsaturated compounds. Examples of such monomers include but are not limited to hydroxypropyl acrylate, (meth)acrylamide, (meth)acrylic acid, dimethylaminoethyl (meth)acrylate, diethylaminoethyl (meth)acrylate, dimethylaminopropyl (meth)acrylamide, diethylaminopropyl (meth)acrylamide and dimethylaminopropyl (meth)acrylate, and their quaternary salts obtained by treating dimethylaminoethyl (meth)acrylate, diethylaminoethyl (meth)acrylate, dimethylaminopropyl (meth)acrylamide, diethylaminopropyl (meth)acrylamide, and dimethylaminopropyl (meth)acrylate with methyl chloride, dimethyl sulfate or benzyl chloride, N-vinyl pyrrolidinone, hydrophobic monomers such as alkyl esters derived from the reactions of alkanols having from 1 to about 16 carbon atoms with ethylenically unsaturated carboxylic acids such as acrylic acid, methacrylic acid, maleic anhydride, fumaric acid, and itaconic acid including ethylhexyl acrylate (EHA), dodecyl(meth)acrylate, octadecyl acrylate, diethyl maleate and hydroxy substituted derivatives of the monomers described above.

More than one monomer can be used to prepare the polymeric thiacrown ethers of the present invention. The preferred monomers in this invention are acrylamide, acrylic acid and hydroxypropyl acrylate.

The polymer portions of the polymeric thiacrown ethers of the present invention can also be obtained by ring-opening polymerization of heterocyclic compounds such as aziridine, epoxide, lactone or lactam. One of the preferred polymers for use in preparing the polymeric thiacrown ethers of this invention is polyethyleneimine (PEI), obtained from the ring-opening polymerization of aziridine. It is commercially available from BASF Corporation under the trade name LUPASOL® (CAS 9002-98-6) with a molecular weight (Mw) of 10,000. However, other lower or higher molecular weight or more crosslinked/branched PEI may also be used for the reaction and are within the scope of the invention. For instance, PEI prepared by the polymerization of aziridine and capped with ethylenediamine (CAS 25987-06-8) or crosslinked with 1,2 dichloroethane (CAS 68130-87-2) can also be utilized in the synthesis of the PEI thiacrown ether containing materials of the present invention. The following formula shows a representative thiacrownpolyalkyleneimine of this invention:

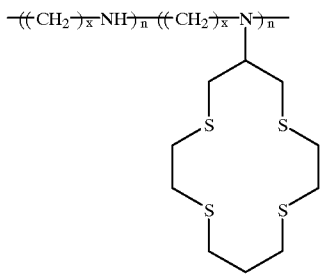

where x=2 to 4 and n=1 to 100,000

Oligomeric polyalkyleneamines are also within the scope of the invention. Some examples are tetraethylenepentamine (TEPA), triethylenetetramine (TETA), diethylenetriamine (DETA), and diethylenetriaminepentaacetic acid (DTPA). One of the preferred polyamines for use in preparing the polymeric thiacrown ethers of this invention is tetraethylenepentamine. The following formula shows a representative oligomeric thiacrownpolyalkyleneimine of this invention:

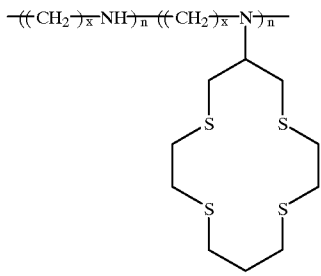

where x=2 to 4 and n=1 to 10.

The polymeric portion of the polymeric thiacrown ethers of this invention can also be prepared by free radical, cationic or anionic polymerization methods in accordance with conventional solution, precipitation, or emulsion polymerization techniques. Polymerization initiators such as azo compounds, persulfates, peroxides, UV light, etc., may be used. Chain transfer agents such as alcohols, amines, or mercapto compounds may be used to regulate the molecular weight of the polymer. Polymers obtained by condensation polymerization techniques such as polyesters or polyamines prepared by the condensation of epichlorohydrin with amines including mono or dialkyl substituted amines are also within the scope of the invention.

The polymeric portion of the polymeric thiacrown ethers of this invention can have linear, branched/crosslinked, block, or graft configurations. Suitable polymers for use in synthesizing the polymeric thiacrown ethers of this invention have number average molecular weights (Mn) of from about 200 to about 1,000,000; preferably from about 500 to about 1,000,000 and most preferably from about 1000 to about 1,000,000. Suitable polymers may be soluble or dispersible in water, or may be soluble or dispersible in organic solvents. The solubility of the polymeric thiacrown ethers of this invention can be varied by the type of monomer, initiator, crosslinking agent, and polymerization method used to create the polymeric portion of the polymeric thiacrown ethers of this invention. For instance, monomers such as acrylic acid, acrylamide, or N-vinylpyrrolidinone could be used to impart water solubility to the invention polymeric thiacrown ethers. Whereas, hydrophobic monomers such as long chain alkyl esters can enhance the solubility of the polymeric thiacrown ethers of this invention in organic solvents.

The thiacrown ether compounds of the present invention are expected to have utility in a wide range of applications including but not limited to metal ion chelating, sequestering, and complexing agents and as corrosion inhibitors for cooling, boiler, and waste water systems, hydrocarbon process systems and metal surface treatments systems.

The following are representative reactions by which the thiacrown ether compounds of this invention can be made. In the following reactions X is independently H; SH; F; Cl; I; substituted or unsubstituted $C_1$ to $C_{10}$ linear or branched alkyl or alkenyl group; substituted or unsubstituted $C_6$ to $C_{10}$ aryl group; amine; mono- or di- $C_1$ to $C_{10}$ lower alkylamino; $C_1$ to $C_5$ lower alkanoylamino; nitro; cyano; COOH; $OCOR_1$ wherein $R_1$ is $C_1$ to $C_{10}$ alkyl or alkenyl group; $OR_2COOR_3$ wherein $R_2$ is substituted or unsubstituted $C_2$ to $C_5$ linear or branched alkyl group and $R_3$ is substituted or unsubstituted $C_1$ to $C_{10}$ linear or branched alkyl group or alkenyl group; $OR_4$ where $R_4$ is substituted or unsubstituted $C_1$ to $C_{10}$ linear or branched alkyl or alkenyl group; $SR_5$ wherein $R_5$ is substituted or unsubstituted $C_1$ to $C_{10}$ linear or branched alkyl or alkenyl group; wherein the substituents of the X moieties are independently OH, SH, F, Br, Cl, I, COOH, amine, mono- or di- $C_1$ to $C_5$ alkylamino, alkanoylamino or nitro. For convenience, the following reactions are described with reference to thiacrown ether compounds containing 4 sulfur atoms, however it is within the scope of this invention that the same types of reactions also can be conducted for thiacrown ether compounds of the present invention having more than 4 sulfur atoms, preferably from 4 to about 10 sulfur atoms and most preferably from 4 to about 6 sulfur atoms.

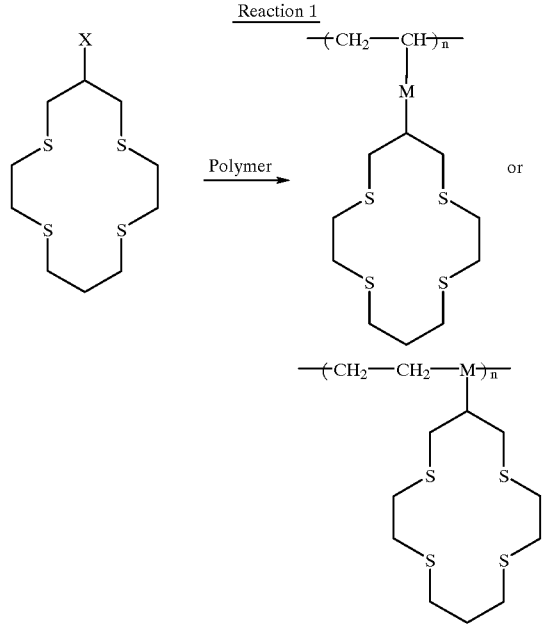

Reaction 1 wherein n is an integer number of monomer repeating unit from 1 to about 100,000 and —COO—, where the carbon atom is attached to the (—CH$_2$—CH—)n group, is an example of the group M. The thiacrown molecule can also be attached to the ethylenically unsaturated or cyclic compounds described herein to form thiacrown functionalized monomers and which can then be polymerized alone or with other monomers as shown in Reaction 2:

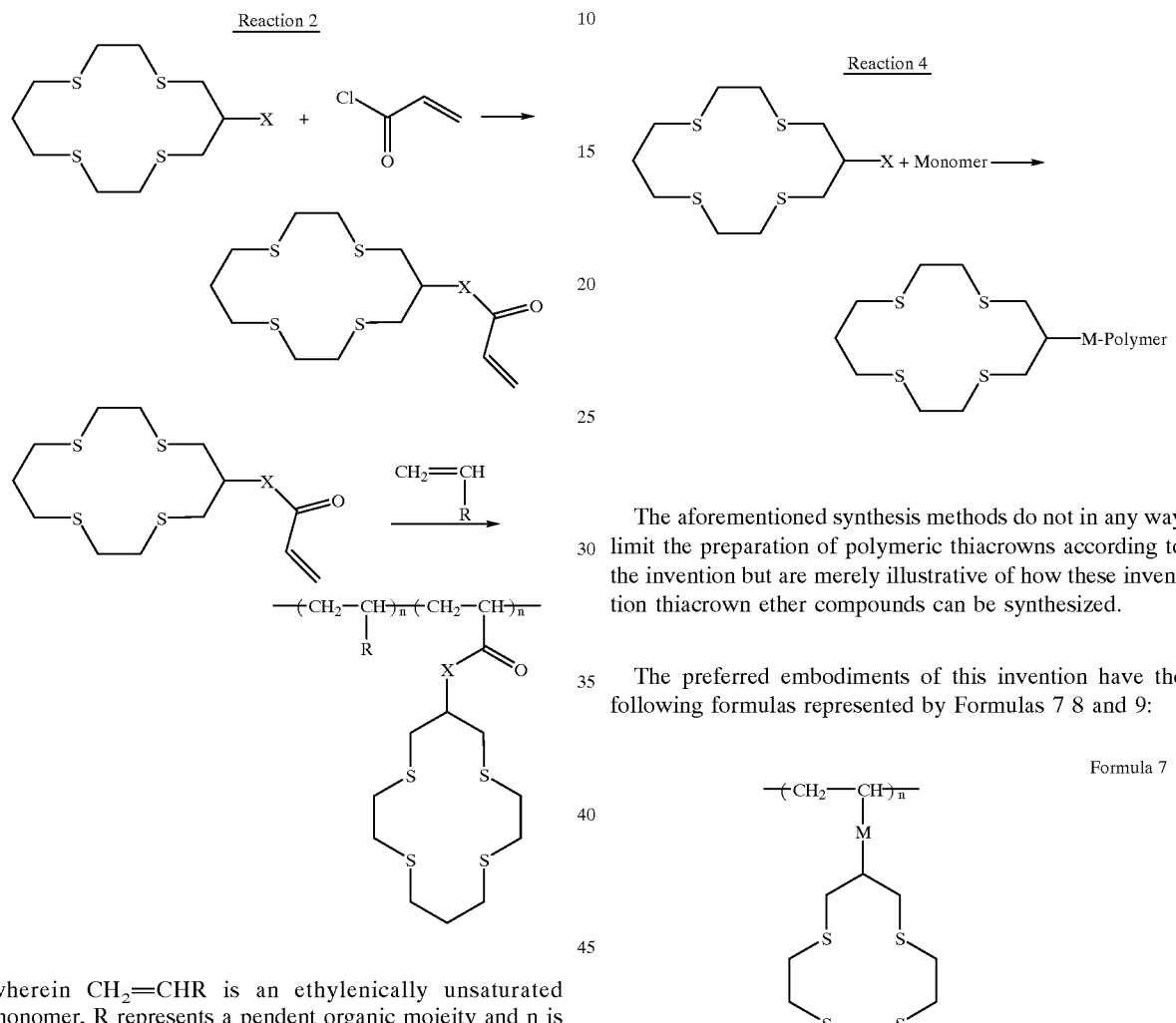

wherein CH$_2$=CHR is an ethylenically unsaturated monomer, R represents a pendent organic moiety and n is an integer number of monomer repeating unit from 1 to about 100,000.

In addition, thiacrown ethers of Formula 2 having X=SH or OH group can be used as a chain transfer agent for polymerization of ethylenically unsaturated monomers wherein the thiacrown can be attached to the polymer directly or by a linkage M as described above, to obtain the desired polymers containing thiacrown ether compounds as shown in Reactions 3 and 4.

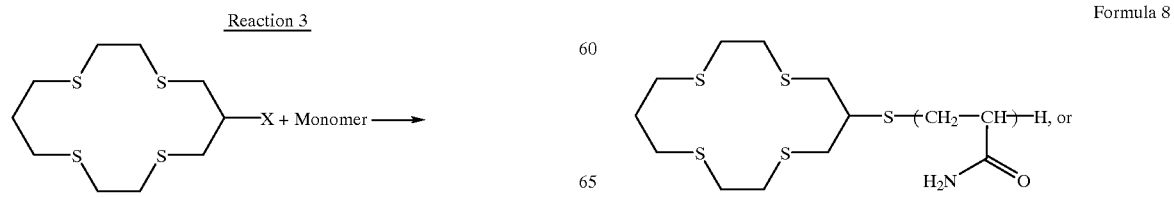

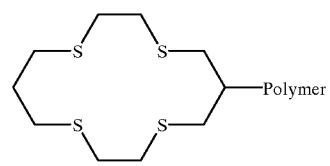

The aforementioned synthesis methods do not in any way limit the preparation of polymeric thiacrowns according to the invention but are merely illustrative of how these invention thiacrown ether compounds can be synthesized.

The preferred embodiments of this invention have the following formulas represented by Formulas 7 8 and 9:

Formula 7

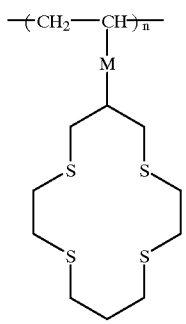

wherein M is preferably CONH; CH$_2$O; or COO where the carbon atom of the COO group is attached to (—CH$_2$—CH—)$_n$, or Formula 8

-continued

Formula 9

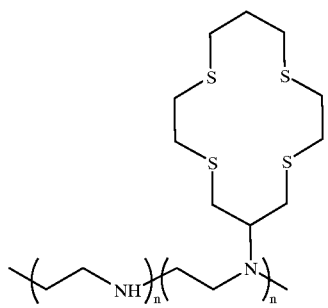

wherein n in Formula 7, 8 and 9 is an integer number of monomer repeating unit from 1 to about 100,000.

The inventors believe that the thiacrown compounds of the present invention are more effective transition metal complexing agents then are crown ether materials. Although not bound by any particular theory, the inventors believe that the different complexing effects of the oxygen in crown ether molecules and the sulfur atoms in the thiacrown molecules of this invention may be explained by Pearson's theory of hard and soft acids and bases. Since oxygen is a hard base, it prefers to complex with hard acids such as alkali and alkali earth cations. In contrast, most of the transition metal cations are softer acids and may not complex well with oxygen donors. Therefore, to complex transition metal cations, a softer donor atom such as nitrogen or sulfur should be more preferable than oxygen.

The inventors also believe that attaching thiacrown molecules to polymer chains or networks enhances the complexing ability of the entire molecule toward metal cations. The neighboring heteroatoms, such as oxygen or nitrogen atoms, along with hydrophobic and inter/intra molecular interactions of the polymers are believed to further stabilize the crown-metal complex. This effect also helps to promote a protective film on the metal surface providing corrosion inhibition. The polymers also enhance the performance of thiacrowns as metal ion chelants or complexing agents for water and process treatments. Since the thiacrown and polymeric thiacrown compounds can form strong complexes with transition metal ions, they can be used for a broad range of applications in water and process treatments, and can be used as catalysts for phase transfer reactions, as encapsulating materials for electronic devices, as corrosion inhibitors and as components of electrorheological fluid, etc. Particularly, the novel thiacrown compounds and polymeric thiacrowns of this invention are expected to be useful as metal ion chelating and complexing agents, as corrosion inhibitors for cooling towers and boilers, as influent water and wastewater treatments, as corrosion inhibitors in electronic packages, as metal extraction materials for mining processes and as metal surface treatments. In addition, depending on the ionic charge, structure and properties of the polymer used during synthesis of the polymeric thiacrowns ethers, the polymeric thiacrowns ethers of this invention are expected to be useful as dispersants, coagulants, flocculants, or film forming agents.

The invention is more particularly described by the following examples, which are to be regarded solely as illustrative, and not as restricting the scope of the invention.

EXAMPLES

Thiacrown compounds containing ten carbon atoms and four sulfur atoms (14-S-4 thiacrown compound where "14" is the total number of atoms in a ring and "4" is the number of sulfur atoms in a ring) in each thiacrown ring moiety are illustrated in the following examples. However, thiacrown compounds having up to 10 sulfur atoms in each thiacrown ring moiety are within the scope of this invention.

Example 1

Synthesis of 1,4,8,11-tetrathia-6-cyclotetradecane bromide.

A 1,4,8,11-tetrathia-6-cyclotetradecanol compound was prepared according to the synthesis disclosed by Masao Tomoi et al. Fifteen grams of the 1,4,8,11-tetrathia-6-cyclotetradecanol compound was mixed in 150 mL of chloroform at room temperature and treated with 16.4 g of thionyl bromide. The reaction was stirred for 4 hours, and then was poured over 100 mL of water. The organic layer was washed three times with 5% sodium carbonate and once with saturated sodium chloride solution. The organic layer was dried over anhydrous magnesium sulfate and then concentrated to yield an oily product weighing 15.1 grams. The identity of the product, having the formula:

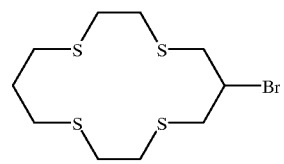

was substantiated as 1,4,8,11-tetrathia-6-cyclotetradecane bromide by $^1$H Nuclear Magnetic Resonance (NMR) {(CDCl$_3$) 67 4.26 (m, 1H), 3.30 (m, 2H), 3.13 (m, 2H), 2.91 (m, 7H), 2.73 (m, 5H), 1.95 (m, 2H)}.

Example 2

Synthesis of 1,4,8,11-tetrathia-6-cyclotetradecanethiol.

A 5.7 gram sample of 1,4,8,11-tetrathia-6-cyclotetradecane bromide from Example 1 was mixed with 1.3 grams of thiourea in 60 mL of 95% ethanol. The mixture was refluxed for 15 hours, before being treated with a solution of 1.0 g of sodium hydroxide in 50 mL of water. The mixture was refluxed for 3 hours. Ethanol was then removed under reduced pressure, and the aqueous solution was acidified with concentrated sulfuric acid to pH 2–3. The acidic solution was extracted three times with methylene chloride. The combined organic layers were dried over magnesium sulfate and then concentrated to give the resulting product as an oil (3.9 g) with 79% yield. The product was identified as:

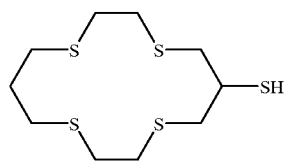

by $^1$H NMR {(CDCl$_3$) 67 3.07 (m, 3H), 2.85 (m, 10H), 2.68 (m, 4H), 1.98 (m, 2H), 1.85 (m, 1H) and IR (NaCl) 2926, 2542 (S—H), 1424, 1201 cm$^{-1}$} and both gas chromatography-mass spectroscopy (GC-MS) and liquid chromatography-mass spectroscopy (LC-MS) analysis revealed that the product had the correct molecular weight of 300.

Example 3

Polymerization of acrylamide in the presence of 1,4,8,11-tetrathia-6-cyclotetradecanethiol and 2,2'-azobis(2,4-dimethylvaleronitrile) (Vazo-52).

A 0.17 gram sample of 1,4,8,11-tetrathia-6-cyclotetradecanethiol from Example 2 was mixed in 15 mL of tetrahydrofuran. This mixture was sparged with nitrogen and heated to 50° C. A 10 mL aliquot of tetrahydrofuran containing 0.07 gram portion of Vazo-52 and 10 mL aliquot of tetrahydrofuran containing 2.0 grams of acrylamide were simultaneously added to the mixture over 2 to 4 hours. The reaction was heated for 2 additional hours after the addition was complete. The product which precipitated during the course of the reaction was filtered from the mixture. The solid precipitate was dissolved in 10 mL of water and added to 200–300 mL of methanol, while stirring, to re-precipitate and purify the product. The product was a white solid weighing 1.3 grams and was identified by $^1$H NMR {(D$_2$O) 67 2.80, 2.25, 2.14, 1.70, 1.58} and $^{13}$C NMR {(D$_2$O) 67 180.0, 179.6, 49.3, 42.2, 36.3, 34.9, 33.0} to have the formula:

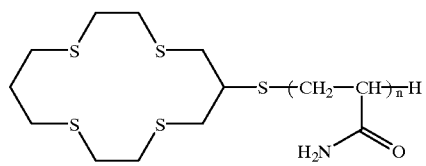

The existence of sulfur in the compound was verified by elemental analysis. In addition, Gel Permeation Chromatography (GPC) indicated the polymeric thiacrown a molecular weight range of about 3,200 to 17,000.

Example 4

Reaction of 1,4,8,11-tetrathia-6-cyclotetradecane bromide with polyethyleneimine (PEI)

A mixture of polyethyleneimine (1.0 g, BASF LUPASOL®, Mw 10,000) and 1,4,8,11-tetrathia-6-cyclotetradecane bromide of Example 1 (0.4–1.2 g) was heated at 50° C. in 20 mL of ethanol for 4–5 hours. After heating, the reaction mixture was treated with 20 mL of water, and the ethanol was removed. The product had a formula of:

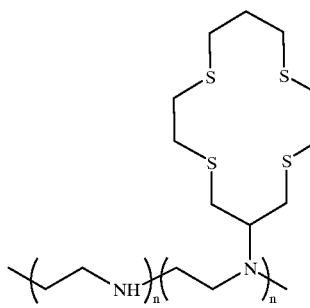

characterized by $^{13}$C NMR (H$_2$O) {67 55.8, 54.7, 53.4, 51.5, 50.6, 48.2, 46.2, 40.3, 38.4, 32.2, 30.4}.

The polyethyleneimine (PEI) used in this example is commercially available from BASF Corporation under the trade name LUPASOL® with a molecular weight (Mw) of 10,000. However, other lower or higher molecular weight or crosslinked/branched PEI can also be used for the reaction and is also within the scope of the invention Example 5

Reaction of 1,4,8,11-tetrathia-6-cyclotetradecane bromide with tetraethylenepentamine.

A mixture of tetraethylenepentamine (1.0 g) and 1,4,8,11-tetrathia-6-cyclotetradecane bromide of Example 1 (2.0 g) was heated at 50° C. in 30 mL of ethanol for 4–5 hours. After heating, the reaction mixture was treated with 30 mL of water, and the ethanol was removed. The product can be represented by the formula:

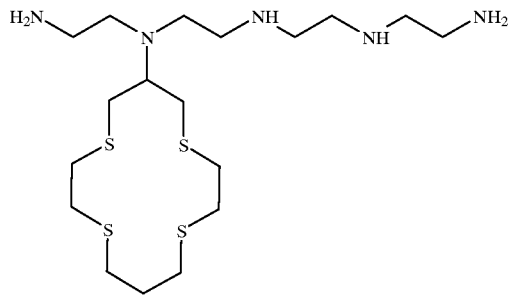

characterized by $^1$H NMR (D$_2$O){67 3.94, 2.72, 2.66, 2.61, 2.46, 1.87} and $^{13}$C NMR (H$_2$O) {67 64.8, 56.4, 52.4, 52.2, 47.9, 47.4, 45.3, 40.8, 39.4, 37.1, 31.9, 31.3, 30.2, 29.9, 24.4}.

Example 6

Synthesis of Thiacrown Acrylate

A 4.0 gram portion of 1,4,8,11-tetrathia-6-cyclotetradecanol was treated with 0.7 grams of sodium hydride in 40 mL of tetrahydrofuran (THF). After mixing for 30 minutes, 1.3 grams of acryloyl chloride was added. The mixture was stirred for 17 hours and then water was added to quench any unreacted sodium hydride. The THF was removed and the aqueous layer was extracted three times with CH$_2$Cl$_2$. The combined organic layers were dried over magnesium sulfate and then concentrated to give 4.0 grams (84% yield) of a waxy solid. The product was characterized by $^1$H NMR (CDCl$_3$){δ 66.48 (dd, 1H), 6.18 (dd, 1H), 5.92 (dd, 1H), 5.18 (m, 1H), 3.01–2.70 (m, 16H), 1.99 (m, 2H)} and identified as:

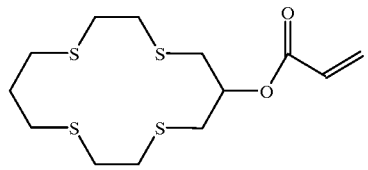

Example 7

Copolymerization of Thiacrown Acrylate with Acrylic Acid.

Twenty grams (20 g) of tetrahydrofuran (THF) was sparged with N$_2$ (gas) while heating to 65° C. Once at 65° C. the sparge was stopped, and a solution of thiacrown acrylate (0.8 g) and acrylic acid (1.7 g) dissolved in 6 g of THF was added via a syringe pump over 4 hours. Another solution containing 1 mole % 2,2'-azobisisbutyronitrile (AIBN) in 5 g THF was added simultaneously via a syringe pump over 4.5 hours. After additions were complete the reaction was held at 65° C. for 2 hours. After cooling reaction to room temperature, the THF was removed under reduced pressure. The product was characterized by $^1$H NMR (CD$_3$OD) {δ 3.1–2.7, 2.5, 2.0–1.7} and $^{13}$C NMR (CD$_3$OD) {67 177.4, 163.9, 67.0, 41.7, 35.2, 31.5, 25.2, 13.5} and identified as:

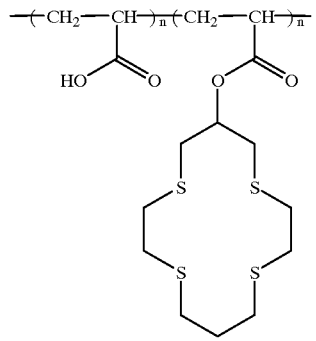

While this invention has been described with respect to particular embodiments thereof, it is apparent that numerous other forms and modifications of the invention will be obvious to those skilled in the art. The appended claims and this invention generally should be construed to cover all such obvious forms and modifications which are within the true spirit and scope of the present invention.

We claim:

1. A thiacrown ether, having the formula:

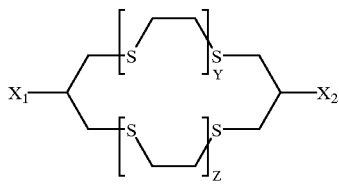

where Y is an integer of 1 to 7 and Z is an integer 1 to 4 with the proviso that Y+Z cannot be greater than 8; $X_1$ and $X_2$ are independently H; SH; F; Cl; I; substituted or unsubstituted $C_1$ to $C_{10}$ linear or branched alkyl or alkenyl group; substituted or unsubstituted $C_6$ to $C_{10}$ aryl; amine; mono- or di-$C_1$ to $C_{10}$ lower alkylamino; $C_1$ to $C_{10}$ lower alkanoylamino; nitro; cyano; COOH; $OCOR_1$ wherein $R_1$ is $C_1$ to $C_{10}$ alkyl or alkenyl group; $OR_2COOR_3$ wherein $R_2$ is substituted or unsubstituted $C_2$ to $C_5$ linear or branched alkyl group and $R_3$ is substituted or unsubstituted $C_1$ to $C_{10}$ linear or branched alkyl group or alkenyl group; $OR_4$ where $R_4$ is substituted or unsubstituted $C_1$ to $C_{10}$ linear or branched alkyl or alkenyl group; or $SR_5$ wherein $R_5$ is substituted or unsubstituted $C_1$ to $C_{10}$ linear or branched alkyl or alkenyl group; wherein the substituents of the $X_1$ and $X_2$ moieties are independently OH, SH, F, Br, Cl, I, COOH, amine, mono- or di-$C_1$ to $C_{10}$ alkylamino, alkanoylamino or nitro and with the proviso that both $X_1$ and $X_2$ cannot both be H; with the proviso that when one of $X_1$ or $X_2$ is H, the other cannot be Cl, unsubstituted octyl, methyl substituted with OH, or methyl substituted with acetoxy; and with the proviso that $R_4$ cannot be methyl substituted with COOH or pentyl substituted with COOH.

2. A polymeric thiacrown ether selected from the group consisting of:

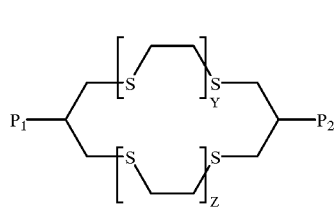

where Y is an integer of 1 to 7 and Z is an integer of 1 to 4 with the proviso that Y+Z cannot be greater than 8 and $P_1$ and $P_2$ are selected from the group consisting of H and polymerized ethylenically unsaturated monomers selected from the group consisting of hydroxypropyl acrylate; (meth)acrylamide; (meth)acrylic acid; dimethylaminoethyl (meth)acrylate; diethylaminoethyl (meth)acrylate; dimethylaminopropyl (meth)acrylamide; diethylaminopropyl (meth)acrylamide; dimethylaminopropyl (meth)acrylate; the quaternary salt of (meth)acrylamide, dimethylaminoethyl (meth)acrylate, diethylaminoethyl (meth)acrylate, dimethylaminopropyl (meth)acrylamide, diethylaminopropyl (meth)acryl-amide and dimethylaminoxypropyl (meth)acrylate; alkyl esters derived from the reactions of alkanols having from 1 to about 16 carbon atoms with ethylenically unsaturated carboxylic acids; and hydroxy substituted derivatives of alkyl esters derived from the reactions of alkanols having from 1 to about 16 carbon atoms with ethylenically unsaturated carboxylic acids;

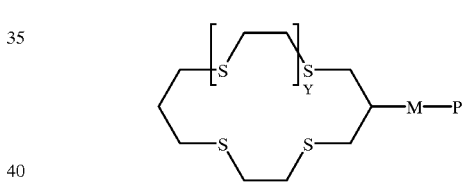

wherein Y is an integer of 1 to 7; wherein M is O; S; COO where the carbon atom is attached to P; $C_1$ to $C_5$ substituted or unsubstituted linear or branched alkylene wherein the substituent is OH, SH, F, Br, Cl, I, COOH, amine, mono- or di- $C_1$ to $C_5$ alkylamino, $C_1$ to $C_3$ lower alkanoylamino or nitro; or M is $NR_6$ where $R_6$ is H or $C_1$ to $C_5$ alkyl; and wherein P is a polymerized ethylenically unsaturated monomer selected from the group consisting of hydroxypropyl acrylate, (meth)acrylamide; (meth)acrylic acid; dimethylaminoethyl (meth)acrylate; diethylaminoethyl (meth)acrylate; dimethylaminopropyl (meth)acrylamide; diethylamino-propyl (meth)acrylamide; dimethylaminoxypropyl (meth)acrylate; the quaternary salt of (meth)acrylamide, dimethylaminoethyl (meth)acrylate, diethylaminoethyl (meth)acrylate, dimethylaminopropyl (meth)acrylamide, diethylaminopropyl (meth)acrylamide and dimethylaminoxypropyl (meth)acrylate; alkyl esters derived from the reactions of alkanols having from 1 to about 16 carbon atoms with ethylenically unsaturated carboxylic acids; and hydroxy substituted derivatives of alkyl esters derived from the reactions of alkanols having from 1 to about 16 carbon atoms with ethylenically unsaturated carboxylic acids; and c)

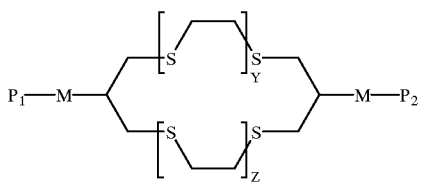

where Y is an integer of 1 to 7 and Z is an integer of 1 to 4 with the proviso that Y+Z cannot be greater than 8; M is independently O; S; COO where the carbon atom is attached to $P_1$ or $P_2$; $C_1$ to $C_5$ substituted or unsubstituted linear or branched alkylene wherein the substituent is OH, SH, F, Br, Cl, I, COOH, amine, mono- or di- $C_1$ to $C_5$ alkylamino, $C_1$ to $C_3$ lower alkanoylamino or nitro; or M is $NR_6$ where $R_6$ is H or $C_1$ to $C_5$ alkyl; and wherein $P_1$ and $P_2$ are independently polymerized ethylenically unsaturated monomers selected from the group consisting of hydroxypropyl acrylate; (meth)acrylamide; (meth)acrylic acid; dimethylaminoethyl (meth)acrylate; diethylaminoethyl (meth)acrylate; dimethylaminopropyl (meth)acrylamide; diethylaminopropyl (meth)acryl-amide; dimethylaminopropyl (meth) acrylate; the quaternary salt of (meth)acrylamide, dimethylaminoethyl (meth)acrylate, diethylaminoethyl (meth) acrylate, dimethylaminopropyl (meth)acrylamide, diethylamino-propyl (meth)acrylamide and dimethylaminopropyl (meth)acrylate; alkyl esters derived from the reactions of alkanols having from 1 to about 16 carbon atoms with ethylenically unsaturated carboxylic acids; and hydroxy substituted derivatives of alkyl esters derived from the reactions of alkanols having from 1 to about 16 carbon atoms with ethylenically unsaturated carboxylic acids.

3. The polymeric thiacrown ether of claim 2 which is thiacrownpolyacrylamide, thiacrownpolyacrylic acid or thiacrownpolyhydroxypropylacrylate.

4. A polymeric thiacrown ether selected from the group consisting of:

a)

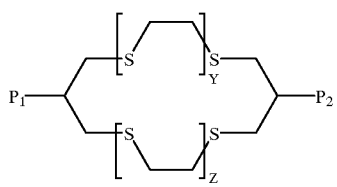

where Y is an integer of 1 to 7 and Z is an integer of 1 to 4 with the proviso that Y+Z cannot be greater than 8 and $P_1$ and $P_2$ are selected from the group consisting of H, polyalkyleneimines and oligomeric polyalkyleneamines;

b)

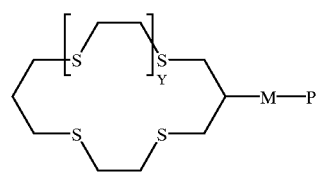

wherein Y is an integer of 1 to 7; wherein P is selected from the group consisting of polyalkyleneimines and oligomeric polyalkyleneamines and wherein M is O; COO where the carbon atom is attached to P; $C_1$ to $C_5$ substituted or unsubstituted linear or branched alkylene wherein the substituent is OH, SH, F, Br, Cl, I, COOH, amine, mono- or di- $C_1$ to $C_5$ alkylamino, $C_1$ to $C_3$ lower alkanoylamino or nitro; or M is $NR_6$ where $R_6$ is H or $C_1$ to $C_5$ alkyl; or M is S with the proviso that P cannot be polyethyleneimine; and c)

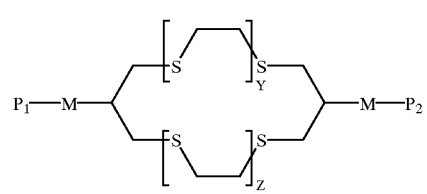

where Y is an integer of 1 to 7 and Z is an integer of 1 to 4 with the proviso that Y+Z cannot be greater than 8; $P_1$ and $P_2$ are selected from the group consisting of H, polyalkyleneimines and oligomeric polyalkyleneamines and wherein M is independently O; COO where the carbon atom is attached to $P_1$ or $P_2$; $C_1$ to $C_5$ substituted or unsubstituted linear or branched alkylene wherein the substituent is OH, SH, F, Br, Cl, I, COOH, amine, mono- or di- $C_1$ to $C_5$ alkylamino, $C_1$ to $C_3$ lower alkanoylamino or nitro; or M is $NR_6$ where $R_6$ is H or $C_1$ to $C_5$ alkyl; or M is S with the proviso that P cannot be polyethyleneimine.

5. The polymeric thiacrown ether of claim 4 wherein M is independently O; COO where the carbon atom is attached to $P_1$ or $P_2$; $C_1$ to $C_5$ substituted or unsubstituted linear or branched alkylene wherein the substituent is OH, SH, F, Br, Cl, I, COOH, amine, mono- or di- $C_1$ to $C_5$ alkylamino, $C_1$ to $C_3$ lower alkanoylamino or nitro; or M is $NR_6$ where $R_6$ is H or $C_1$ to $C_5$ alkyl and said polyalkyleneimine is polyethyleneimine.

6. The polymeric thiacrown ether of claim 4 wherein said oligomeric polyalkyleneamines are selected from the group consisting of tetraethylenepentamine, triethylenetetramine, diethylenetriamine and diethylenetriaminepentaacetic acid.

7. A polymeric thiacrown ether having the formula:

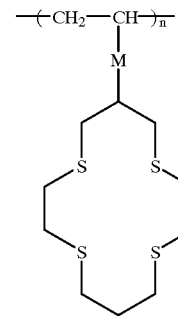

wherein M is CONH; $CH_2O$; or COO where the carbon atom is attached to $(-CH_2-CH-)_n$ and wherein n is an integer number of monomer repeating unit from 1 to about 100,000.

8. A polymeric thiacrown ether having the formula:
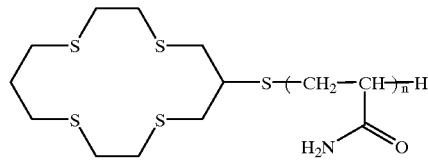
wherein n is an integer number of monomer repeating unit from 1 to about 100,000.
9. A polymeric thiacrown ether having the formula:
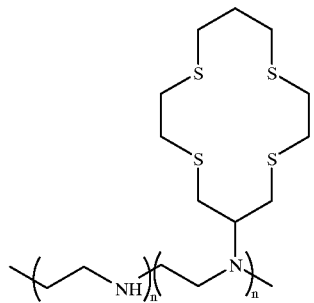
wherein n is an integer number of monomer repeating unit from 1 to about 100,000.
* * * * *